United States Patent [19]

Brahm et al.

[11] Patent Number: 5,459,214
[45] Date of Patent: Oct. 17, 1995

[54] OLEFINICALLY UNSATURATED ISOCYANATES

[75] Inventors: Martin Brahm, Engelskirchen; Eberhard Arning, Kaarst; Lutz Schmalstieg, Köln; Bernd Riberi, Odenthal, all of Germany

[73] Assignee: Bayer Aktiengesellschaft, Leverkusen, Germany

[21] Appl. No.: 195,726

[22] Filed: Feb. 11, 1994

[30] Foreign Application Priority Data

Feb. 19, 1993 [DE] Germany ............. 43 05 162.6

[51] Int. Cl.$^6$ .................................... C08F 26/02
[52] U.S. Cl. ............................ 526/301; 526/312
[58] Field of Search .................... 526/301, 312

[56] References Cited

U.S. PATENT DOCUMENTS 4,225,695  9/1980  Schuster et al. ............. 528/75

FOREIGN PATENT DOCUMENTS

| | | |
|---|---|---|
| 2309902 | 10/1991 | Canada . |
| 301345 | 2/1989 | European Pat. Off. . |
| 301345 | 2/1989 | European Pat. Off. . |
| 1495983 | 3/1969 | Germany . |
| 2726900 | 1/1979 | Germany . |
| 1309045 | 3/1973 | United Kingdom . |

OTHER PUBLICATIONS

4th Edition, vol. 19, pp. 75–80 Verlag Chemie Weinheim, Deerfield Beach, Fla. Basle, 1980.

*Primary Examiner*—Joseph L. Schofer
*Assistant Examiner*—Wu C. Cheng
*Attorney, Agent, or Firm*—Joseph C. Gil; Thomas W. Roy

[57] ABSTRACT

The present invention relates to olefinically unsaturated, urethane group-containing isocyanates which are prepared by reacting at an NCO/OH equivalent ratio of 4 to 40
a) an isocyanate component substantially containing urethane group-free cycloaliphatic diisocyanates with
b) an unsaturated alcohol component substantially containing monohydric olefinically unsaturated alcohols
and subsequently removing distillable unreacted isocyanates by distillation. The present invention also relates to a process for the preparation of these isocyanates and to their use as a binder component in one-component, coating compositions which may be cured at room temperature.

6 Claims, No Drawings

OLEFINICALLY UNSATURATED ISOCYANATES

BACKGROUND OF THE INVENTION

1. Field of the Invention

The present invention relates to a process for the preparation of olefinically unsaturated isocyanates from certain, preferably cycloaliphatic, polyisocyanates and certain olefinically unsaturated, preferably monohydric, alcohols; the isocyanates obtained in accordance with this process; and their use as a binder component in one-component coating compositions.

2. Description of the Invention

One-component coating compositions based on prepolymers containing NCO-functional urethane groups are known (Houben Weyl, Methoden der Organischen Chemie [Organic chemistry methods], Vol. E 20, page 1646, Georg Thieme Verlag 1987). They are prepared by reacting organic polyisocyanates with high molecular weight, high functionality polyols, in particular polyether polyols and/or polyester polyols. The high molecular weight provides these compositions with good film-forming properties and results in good optical properties for the film. The high molecular weight also results in higher viscosity, which means that the prepolymers can only be utilized as paints or in coating compositions if they are greatly diluted or contain a considerable proportion of monomeric diisocyanate.

High monomeric diisocyanate concentrations are, however, physiologically unacceptable. The utilization of large quantities of solvent is also not acceptable for environmental reasons. The gap between a high molecular weight, high functionality prepolymer having a high viscosity but providing excellent properties, on the one hand, and low molecular weight, low viscosity products having unsatisfactory solution stability and drying properties, on the other hand, cannot be closed with the NCO-functional prepolymers.

In addition to NCO-functional coating resins, one-component systems which can be cross-linked by oxidation are also known (Ullmann, Enzyklopädie der technischen Chemie [Encyclopaedia of industrial chemistry], 4th edition, Vol. 19, pages 75 et seq., Verlag Chemie Weinheim, Deerfield Beach Fla., Basle 1980). These polymeric compounds may additionally also contain urethane groups (DE-OS 4,011,376). If these urethane resins which cross-link by oxidation have higher molecular weights, relatively fast-drying, tough paint systems result. However, considerable quantities of solvent or reactive thinner are required for these resins.

Admittedly, reactive thinners such as those described in EP-A 0,301,345 exhibit, without solvent, relatively low viscosities, but they must be used in combination with considerable quantities of high molecular weight compounds, such as alkyd resins, to obtain workable coating compositions. Their film-forming properties when they are used as the only resin component are totally unsatisfactory, and the low molecular weight structure results in unsatisfactory and excessively slow drying.

Ester group-containing reactive thinners, such as those described in EP-A 0,301,345, are unsuitable for applications in the construction sector, because there is a danger that the ester group, which is highly vulnerable to hydrolysis, will rapidly dissociate on basic substrates such as concrete.

An object of the present invention is to provide low-viscosity resins for solvent free or low solvent-containing coating compositions which have good technical properties and rapid chemical drying at room temperature and which may be applied in a universal and physiologically acceptable manner.

This object may be achieved using the process according to the invention which is described below in greater detail. The resulting products satisfy the requirements for the simultaneous presence of olefinic double bonds, urethane groups and isocyanate groups. For this a balanced ratio of urethane groups, isocyanate groups and double bonds which may be cross-linked by oxidation is particularly essential.

SUMMARY OF THE INVENTION

The present invention relates to a process for the preparation of olefinically unsaturated, urethane group-containing isocyanates having an NCO content of 4 to 20 wt-% and an average NCO functionality of 0.6 to 1.5 by reacting at an NCO/OH equivalent ratio of 4 to 40, optionally in the presence of catalysts for the NCO/OH addition reaction, a) an isocyanate component having an NCO content of 20 to 56 wt-% and an average NCO functionality of less than 2.5, and containing
  a1) 80 to 100 wt-% of urethane group-free, cycloaliphatic diisocyanates having an NCO content of 25 to 56 wt-% and
  a2) 0 to 20 wt-% of other organic polyisocyanates having an NCO content of 10 to 50 wt-%
with
b) an olefinically unsaturated alcohol component having an average hydroxyl functionality of less than 1.5 and an iodine number greater than 70, and containing
  b1) 80 to 100 wt-% of monohydric olefinically unsaturated alcohols or mixtures of such alcohols having an average of 10 to 22 carbon atoms per molecule and
  b2) 0 to 20 wt-% of other mono- or polyhydric alcohols having a molecular weight of 32 to 326, and subsequently removing excess, distillable isocyanate component a) from the reaction product by distillation until the maximum content of these diisocyanates is 0.5 wt-%.

The present invention also relates to the olefinically unsaturated isocyanates which are obtained in accordance with this process and to their use as the binder in one-component coating compositions which may be cured at room temperature.

DETAILED DESCRIPTION OF THE INVENTION

Even though EP-A 0,301,345 describes isocyanate group-containing reaction products of organic diisocyanates with unsaturated alcohols, these are isocyanate group-containing reaction products of short chain alcohols which, without removal of unreacted starting diisocyanates, are reacted completely with polyols to form esters. The resulting olefinically unsaturated compounds which are substantially free from isocyanate groups do not possess satisfactory drying properties and have a tendency to crystallize.

The products according to the invention preferably have an NCO content of about 6 to 13 wt-%, an average NCO functionality of about 0.7 to 1.3, an iodine number of about 20 to 250, a viscosity at 23° C. of about 100 to 5000 mPa/s and a content of distillable monomeric isocyanates of less than 0.2 wt-%.

In accordance with the invention cycloaliphatic diisocyanates a1) or mixtures of cycloaliphatic diisocyanates a1) with other organic polyisocyanates a2) are utilized as isocyanate component a). Component a2) is present, if at all, in quantities of up to 20, preferably up to 10 wt-%, based on the total weight of component a).

The term "cycloaliphatic diisocyanates" is understood to mean diisocyanates containing at least one cycloaliphatic ring in which the NCO groups are bonded exclusively to aliphatic or cycloaliphatic carbon atoms. The cycloaliphatic diisocyanates a1) have an NCO content of 25 to 56 wt-%, preferably 30 to 50 wt-%. Examples of suitable cycloaliphatic diisocyanates for use as component a1) include 1,3-diisocyanatocyclopentane, 1,3- and 1,4-diisocyanato cyclohexane, 1-methyl-2,4-diisocyanato cyclohexane, 1-methyl-2,6-diisocyanato cyclohexane, the isomeric diisocyanato dicyclohexyl methanes, 2,5- and 2,6-bis(isocyanatomethyl)dicyclo[2.2.1]-heptane, 4-isocyanatomethyl-1-methyl-cyclohexyl isocyanate (IMCI), 1-isocyanato-3,3,5-trimethyl-5-isocyanatomethyl cyclohexane (IPDI), 1,3- or 1,4-bis(dimethyl-isocyanatomethyl)cyclohexane and mixtures of these isocyanates. IPDI is preferably used as component a1).

Starting isocyanates a2), which may be used in minor quantities to obtain specific properties, have an NCO content of 10 to 50 wt-%. Examples include aliphatic diisocyanates such as 1,6-diisocyanatohexane (HDI) or 2,2,4-triethyl-1,6-diisocyanatohexane and aromatic diisocyanates such as 2,4- and/or 2,6-diisocyanatotoluene or the isomeric diphenylmethane diisocyanates. Preferred polyisocyanates a2) are modification products of the preceding polyisocyanates which have biuret, uretdione and/or isocyanurate groups. The modified polyisocyanates may be obtained by biuretizing, dimerizing and/or trimerizing a portion of the isocyanate groups of the diisocyanates which have previously been described for use as component a1) or b2). These modification reactions may be terminated at any time so as to give mixtures a) of the individual components a1) and a2) in the amounts specified.

Most preferably, component a) is exclusively based on cycloaliphatic diisocyanates a1), more particularly IPDI.

Component b) preferably exhibits a hydroxyl functionality of 1 to 1.5, preferably 1, and an iodine number greater than 90, preferably from 100 to 400.

Component b) takes the form of olefinically unsaturated alcohols b1) or mixtures thereof with up to 20 wt-%, preferably up to 10 wt-%, of other alcohols b2). Component b) preferably exclusively contains unsaturated alcohols b1).

Suitable alcohols b1) include olefinically unsaturated alcohols or mixtures of olefinically unsaturated alcohols having an average of 10 to 22, preferably 14 to 20 carbon atoms per molecule and an iodine number greater than 70, preferably greater than 90, and more preferably 100 to 400. Monohydric alcohols or alcohol mixtures derived from the corresponding unsaturated synthetic or natural fatty acids or fatty acid mixtures are highly suitable. Examples include those obtained by reduction to the corresponding alcohols of unsaturated carboxylic acids such as dodecenoic acid, tetradecenoic acid, hexadecenoic acid, octadecenoic acid, eicosenoic acid, docosenoic acid, 12-oxyoctadecenoic acid, octadecadienoic acid, octadecatrienoic acid, eicosatetraenoic acid, docosapentaenoic acid, decenoic acid and mixtures of such acids.

The other alcohols b2) which may optionally be used are those having a molecular weight of 32 to 326, preferably 74 to 286. Both saturated monohydric and also polyhydric alcohols are suitable. Examples include methanol, ethanol, n-propanol, isopropanol, the isomeric butanols, pentanols or hexanols, n-octanol, n-dodecanol or n-octadecanol. Also suitable are saturated fatty alcohols or polyhydric alcohols such as ethylene glycol, propylene glycol, the isomeric butanediols, hexanediols or octanediols, glycerol, trimethyiolpropane and mixtures of any of the preceding alcohols. If alcohols b2) are utilized, they are used in amounts within the disclosed ranges such that the required functionality of component b) is obtained.

Components a) and b) are reacted together in quantities which are sufficient to provide an NCO/OH equivalent ratio of 4:1 to 40:1, preferably 5:1 to 20:1 and more preferably 6:1 to 12:1. The reaction generally takes place within the temperature range 10° to 140° C., preferably 40° to 100° C. The reaction may optionally be conducted in the presence of known catalysts such as triethylamine, triethylenediamine, dimethylbenzylamine, tin(II)octoate, tin(II)ethylhexanoate or dibutyl zinc dilaurate.

Following the reaction, the excess, distillable starting diisocyanate is removed by distillation, preferably by thin-film evaporation, to obtain a product containing less than 0.5, preferably less than 0.2 wt-%, of residual starting diisocyanate.

The products according to the invention are valuable binders for coating compositions which are curable under the influence of atmospheric humidity and atmospheric oxygen.

In addition to the products according to the invention, the coating compositions may also contain known catalysts for the oxidative cross-linking reaction. Such catalysts are listed, for example, in Ullmann, Enzyklopädie der technischen Chemie, 4th edition, Vol. 23, page 42 (drying substances). Verlag Chemie 1983, and in Offenlegungsschrift DE 4 032 546 and publications cited therein. Examples include cobalt, lead, magnesium, zirconium, aluminum, manganese, calcium, cerium, copper, nickel, vanadium, barium and zinc siccatives and mixtures thereof.

Catalysts to speed up the isocyanate addition reaction, such as those previously set forth, may also be added to the products according to the invention.

For the purpose of obtaining a specific property profile in the coating compositions, it may be appropriate to use as further resin components other non-functional polymers or NCO-functional additives and polymer components which are capable of oxidative cross-linking. These additional resin components are generally used in a maximum quantity of 30, preferably 10 wt-%. Preferably, such additional resin components are not used.

Examples of additional resin components include alkyd resins such as those described in Römpps Chemie-lexikon, Vol. 1, page 202, Frankh'sche Verlagsbuchhandlung, Stuttgart, 1966, or in D. H. Solomon, The Chemistry of Organic Filmformers, pages 75 to 101, John Wiley & Sons Inc., New York 1967. NCO-functional resins which may be utilized in addition to the products according to the invention include the known lacquer polyisocyanates, which are preferably derivatives of aliphatic diisocyanates, more preferably 1,6-diisocyanatohexane, which contain (i) urethane groups, (ii) isocyanurate and/or uretdione groups or (iii) biuret groups.

In addition to the products according to the invention and the additional resin components previously set forth, the coating compositions may also contain other additives. Examples of these additives include solvents, which may be present in amounts such that the solids content of the coating compositions is greater than 85, preferably greater than 90 wt-%. More preferably, solvents are not used. Examples of suitable solvents include toluene, xylene, cyclohexane, chlorobenzene, butyl acetate, ethyl acetate, ethyl glycol acetate, pentyl acetate, hexyl acetate, methoxypropyl acetate, tetrahydrofuran, dioxane, acetone, methyl ethyl ketone, xylene, white spirits, higher aromatics such as those available commercially under the names Solvesso or Shellsol, and mixtures of these solvents. Isoparaffinic solvents having low odor, such as those available under the names Isopar or Nappar are particularly suitable. The products according to the invention exhibit good compatibility and miscibility with these non-polar solvents despite the polar urethane groups.

Known wetting agents, flow improvers, anti-skinning agents, defoaming agents, matting agents such as silicic acid, aluminum silicates and high-boiling waxes, viscosity regulators, pigments, dyes, UV absorbing agents and stabilizers to counter thermal or oxidative decomposition may also be utilized as additives in the coating compositions according to the invention.

The coating compositions according to the invention may be used for coating any substrate such as wood, plastics, leather, paper, textiles, glass, ceramic, plaster, masonry, metals or concrete. They may be applied by conventional methods such as spraying, brushing, flow-coating, pouring, dip coating or rolling. The coating compositions may be used in the form of transparent varnishes as well as in the pigmented form of paints.

The coatings may be cured at 20° C. generally within a period of 2 to 24 hours to form high-grade coatings. Hardening may, however, also take place at lower temperatures (to −5° C.) or in accelerated manner at higher temperatures (for example 130° C.).

In the following examples all parts and percentages are by weight unless otherwise indicated.

EXAMPLES

Examples 1 to 5 (according to the invention)

The quantities of isocyanate set forth in Table 1 below were reacted in a nitrogen-swept, stirred apparatus with the quantity of alcohol set forth. The dewatered alcohol component was added dropwise at 80° C. to the isocyanate component. The theoretical NCO content was reached after a reaction time of 3 to 5 hours in a nitrogen atmosphere. The excess diisocyanate was subsequently separated, if necessary, by means of thin-film distillation under high vacuum (0.1 to 0.3 mbar) at a temperature of 150° C. The characteristic data for the products is also set forth in Table 1.

TABLE 1

| Example No. | Isocyanate Quantity, equiv. | Alcohol Quantity, equiv 18° C. | NCO % | Viscosity (23° C.) mPa · s | Free diisocyanate % |
| --- | --- | --- | --- | --- | --- |
| 1[1] | 10 IPDI | 1 Ocenol 110/130[2] | 8.48 | 700 | 0.10 |
| 2 | 7 IPDI | 1 Ocenol 110/130 | 8.14 | 800 | 0.04 |
| 3 | 10 IPDI | 1 Ocenol 110/130 0.3 TMP | 8.8 | 2100 | 0.49 |
| 4 | 10 diisocyanato-dicyclohexyl-methane | 1 Ocenol 110/130 | 7.54 | 1500 | 0.03 |
| 5 | 8 trimerized IPDI[3] | 1 Ocenol 110/130 | 9.37 | 3500 | 0.05 |

[1] Analysis by gel permeation chromatography indicates that the product contained 85% NCO-functional monourethane compound.
[2] Ocenol 110/130 is a technical mixture of monohydric olefinically unsaturated alcohols available from Henkel and having an average of 18 carbon atoms per molecule and an iodine number of 110 to 130.
[3] Trimerization of the diisocyanate was initiated with a 0.2 mmol methylcholine solution (10% concentration) from an initial NCO content of 37.8% to an NCO content of 34.5% at 55° C., and stopped with 0.2 mmol dibutyl phosphate (theoretical functionality: 2.07). It was a mixture of approx. 82 wt-% IPDI with approx. 18 wt-% IPDI trimer.

Examples 6 to 12 (Comparative Examples)

Table 2 below set forth comparative products prepared analogously to Examples 1 to 5, which, as may be seen from Table 2, exhibit a consistency which is unsuitable for use according to the invention or which, as can be seen from Table 4, exhibit unsatisfactory drying properties.

TABLE 2

| Example No. | Isocyanate Quantity, equiv. | Alcohol Quantity, equiv | NCO % | Viscosity (23° C.) mPa · s | Free diisocyanate % |
| --- | --- | --- | --- | --- | --- |
| 6[1] | 1 IPDI | 1 Ocenol 110/130 | <0.5 | 3300 | — |
| 7 | 2 IPDI | 1 Ocenol 110/130 | 6.3 | 1000 | 0.04 |
| 8 | 10 IPDI | 1 Ocenol 60/65[2] | 8.41 | 650 | 0.08 |
| 9 | 8 IPDI | 1 2-ethyl-1,3-diol | 11.5 | resinous | 0.03 |
| 10[1] | 1 diisocyanatodi-cyclohexylmethane | 1 Ocenol 110/130 | <0.5 | paste | — |
| 11[1] | 1 1,6-hexamethylene- | 1 Ocenol 110/130 | — | solid | — |

TABLE 2-continued

| Example No. | Isocyanate Quantity, equiv. | Alcohol Quantity, equiv | NCO % | Viscosity (23° C.) mPa · s | Free diiso-cyanate % |
|---|---|---|---|---|---|
| 12[1) | diisocyanate 1 2,4-tolylene diiso-cyanate | 0.5 Ocenol 110/130 | 7.5 | crystalline | — |

[1)Product not subjected to thin-film distillation.
[2)Technical mixture of monohydric olefinically unsaturated alcohols having an iodine number of 60 to 65 and containing 12 to 20 carbon atoms per molecule; manufactured by Henkel, Düsseldorf.

Examples 13 to 16 (use according to the invention)

Transparent varnishes having the following composition were prepared using the resins according to the invention set forth in Table 3 below (the siccatives used in these examples and in example 20 are sales products of Borchers AG, Germany):

93.4 parts resin 2.8 parts Octa Soligen Calcium 4 siccative 0.5 parts Octa Soligen Cobalt 6 siccative 2.8 parts Octa Soligen Zirconium 18 siccative 0.5 parts methylethylketoxime (anti-skinning agent)

The varnishes were applied to cleaned glass plates in a film thickness of 120 μm and were cured at room temperature. The resulting drying times (time until sand-dry, in hours at 20° C.), resistance to pressure (to DIN 53150), pendulum damping values (to DIN 53157) and solvent resistance (0=unchanged, 5=dissolved) are set forth in Table 3 below.

TABLE 3

| No. | Resin from Example | Hours until sand-dry | Hours until pressure-dry | Pendulum damping after 7 days (sec.) | Solvent resistance |
|---|---|---|---|---|---|
| 13 | 1 | 4.5 | >8<18 | 70 | 1–2 |
| 14 | 2 | 4.5 | >8 <18 | 55 | 1–2 |
| 15 | 3 | 4.0 | >8 <18 | 60 | 1–2 |
| 16 | 5 | 3.5 | >8 <18 | 70 | 1 |

Examples 17 to 19 (for comparison)

In Examples 17 to 19 comparative formulations were prepared analogously to Examples 13 to 16, using the products of Comparative Examples 6 to 8. The poor drying properties are apparent from the data set forth in Table 4 below.

TABLE 4

| Example No. | Resin from Comparative Example | Hours until sand-dry | Hours until pressure-dry | Pendulum damping after 7 days (sec.) |
|---|---|---|---|---|
| 17 | 6 | >24 | >72 | 8 |
| 18 | 7 | >24 | >72 | 11 |
| 19 | 8 | >24 | >48 | 17 |

Example 20 (pigmented paint according to the invention)

Using the resin from Example 1 a base formulation for pigmented paints having the following composition was prepared:

74.0 parts resin from Example 1

2.2 parts Octa Soligen Calcium 4 siccative 18.6 parts Bayertitan R-KB-5 pigment 2.2 parts toluenesulphonyl isocyanate 0.4 parts Octa Soligen Cobalt 6 siccative 2.2 parts Octa Soligen Zirconium 18 siccative 0.4 parts methylethylketoxime.

A 120 μm-thick film applied to a cleaned glass plate was sand-dry after 4 hours at 23° C., and was thoroughly dry after 18 hours. A solvent-resistant high gloss painted surface was obtained.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the preparation of olefinically unsaturated, urethane group-containing isocyanates having an NCO content of 4 to 20 wt-% and an average NCO functionality of 0.6 to 1.5 by reacting at an NCO/OH equivalent ratio of 4:1 to 40:1, optionally in the presence of catalysts for the NCO/OH addition reaction, a) an isocyanate component having an NCO content of 20 to 56 wt-% and an average NCO functionality of less than 2.5, and containing a1) 80 to 100 wt-% of one or more urethane group-free, cycloaliphatic diisocyanates having an NCO content of 25 to 56 wt-% and a2) 0 to 20 wt-% of one or more other organic polyisocyanates having an NCO content of 10 to 50 wt-% with b) an olefinically unsaturated alcohol component having an average hydroxyl functionality of less than 1.5 and an iodine number greater than 70, and containing b1) 80 to 100 wt-% of one or more monohydric olefinically unsaturated alcohols having an average of 10 to 22 carbon atoms per molecule and b2) 0 to 20 wt-% of one or more other mono- or polyhydric alcohols having a molecular weight of 32 to 326, and subsequently removing excess, distillable isocyanate component a) from the reaction product by distillation until the maximum content of these diisocyanates is 0.5 wt-%.

2. The process of claim 1 wherein isocyanate component a) contains 100 wt-% of cycloaliphatic diisocyanates a1).

3. The process of claim 1 wherein isocyanate component a) contains 100 wt-% of 1-isocyanato-3,3,5-trimethyl-5-isocyanatomethyl cyclohexane.

4. The process of claim 1 wherein component b) contains 100 wt-% of one or more fatty alcohols having 14 to 20 carbon atoms and an average iodine number greater than 90.

5. The process of claim 2 wherein component b) contains 100 wt-% of one or more fatty alcohols having 14 to 20 carbon atoms and an average iodine number greater than 90.

6. The process of claim 3 wherein component b) contains 100 wt-% of one or more fatty alcohols having 14 to 20 carbon atoms and an average iodine number greater than 90.

* * * * *